US012023395B2

(12) United States Patent
Tsaur et al.

(10) Patent No.: US 12,023,395 B2
(45) Date of Patent: Jul. 2, 2024

(54) XANTHAN STRUCTURED HIGH POLYOL LIQUID CLEANSERS

(71) Applicant: Conopco, Inc., Englewood Cliffs, NJ (US)

(72) Inventors: Sheng Liang Tsaur, Norwood, NJ (US); Lin Yang, Woodbridge, CT (US)

(73) Assignee: CONOPCO, INC., Englewood Cliffs, NJ (US)

( * ) Notice: Subject to any disclaimer, the term of this patent is extended or adjusted under 35 U.S.C. 154(b) by 1 day.

(21) Appl. No.: 16/480,764

(22) PCT Filed: Jan. 4, 2018

(86) PCT No.: PCT/EP2018/050207
§ 371 (c)(1),
(2) Date: Jul. 25, 2019

(87) PCT Pub. No.: WO2018/145827
PCT Pub. Date: Aug. 16, 2018

(65) Prior Publication Data
US 2019/0388314 A1    Dec. 26, 2019

(30) Foreign Application Priority Data

Feb. 8, 2017  (EP) .................................... 17155142

(51) Int. Cl.
| | | |
|---|---|---|
| *A61K 8/34* | (2006.01) | |
| *A61K 8/362* | (2006.01) | |
| *A61K 8/73* | (2006.01) | |
| *A61Q 19/10* | (2006.01) | |

(52) U.S. Cl.
CPC .............. *A61K 8/345* (2013.01); *A61K 8/362* (2013.01); *A61K 8/73* (2013.01); *A61Q 19/10* (2013.01); *A61K 2800/41* (2013.01); *A61K 2800/5422* (2013.01); *A61K 2800/5424* (2013.01); *A61K 2800/5426* (2013.01); *A61K 2800/5428* (2013.01); *A61K 2800/80* (2013.01)

(58) Field of Classification Search
CPC .......... A61K 8/345; A61K 8/362; A61K 8/73; A61K 2800/41; A61K 2800/5422; A61K 2800/5424; A61K 2800/5426; A61K 2800/5428; A61K 2800/80; A61Q 19/10
See application file for complete search history.

(56) References Cited

U.S. PATENT DOCUMENTS

| | | |
|---|---|---|
| 4,728,457 A | 3/1988 | Fieler et al. |
| 4,788,006 A | 11/1988 | Bolich, Jr. et al. |
| 5,716,919 A | 10/1998 | Sano |
| 5,948,739 A | 9/1999 | Inman |
| 6,001,344 A | 12/1999 | Villa |
| 6,303,108 B1 | 10/2001 | Roulier et al. |
| 6,387,857 B2 | 5/2002 | Chambers et al. |
| 7,879,780 B2 | 2/2011 | Tsaur |
| 7,910,090 B2 | 3/2011 | Dueva-Koganov |
| 2001/0001783 A1 | 5/2001 | Nystrand et al. |
| 2003/0108576 A1* | 6/2003 | Bielli .................... A61K 8/678 424/401 |
| 2004/0121925 A1 | 6/2004 | Harmalker |
| 2006/0183662 A1 | 8/2006 | Crotty et al. |
| 2007/0098662 A1 | 5/2007 | Blume et al. |
| 2010/0075881 A1 | 3/2010 | Tsaur |
| 2011/0245124 A1 | 10/2011 | Tsaur et al. |
| 2016/0008255 A1 | 1/2016 | Ferry et al. |
| 2016/0151255 A1 | 6/2016 | You et al. |
| 2018/0221259 A1* | 8/2018 | Potanin ................... A61K 8/44 |
| 2020/0022891 A1 | 1/2020 | Yang et al. |

FOREIGN PATENT DOCUMENTS

| | | |
|---|---|---|
| CN | 1303268 | 7/2001 |
| CN | 1339961 | 3/2002 |
| CN | 101160154 | 4/2008 |
| CN | 101862275 | 10/2010 |
| CN | 102078280 | 6/2011 |
| CN | 103356408 | 10/2013 |
| CN | 104257521 | 1/2015 |
| CN | 104800091 | 7/2015 |
| CN | 104971011 | 10/2015 |
| CN | 105078776 | 11/2015 |
| CN | 105163705 | 12/2015 |
| EP | 0194097 | 10/1986 |
| EP | 0559375 | 9/1993 |
| EP | 1000606 | 5/2000 |
| EP | 1029532 | 8/2000 |
| EP | 1237534 | 1/2005 |

(Continued)

OTHER PUBLICATIONS

Huang, X. et al., Hydrocolloids in emulsions: particle size distribution and interfacial activity, 2001, Food Hydrocolloids, vol. 15, pp. 533-542. (Year: 2001).*
Naturallythinking, screenshot of Xanthan Gum Clear from Wayback machine, 2020, from https://web.archive.org/web/20200923200714/https://naturallythinking.com/xanthan-gum-clear (Year: 2020).*
Dannystanzl, Formulating a light moisture cream with Xanthan and Emulsifiers, 2017, from https://naturalblog.co/2017/11/16/formulating-light-cream-xanthan-emulsifiers/ (Year: 2017).*
Search Report and Written Opinion in EP17155142; May 23, 2017.

(Continued)

*Primary Examiner* — Bethany P Barham
*Assistant Examiner* — Ayaan A Alam
(74) *Attorney, Agent, or Firm* — Krista J. Aiello

(57) ABSTRACT

The invention relates to high polyol compositions comprising foaming, preferably mild surfactants. While xanthan gum is normally incompatible with such composition, applicants have surprisingly found compositions (having specified particles size) and process for making such compositions such that xanthan gum can now be used as structurant.

11 Claims, No Drawings

(56) References Cited

FOREIGN PATENT DOCUMENTS

| | | |
|---|---|---|
| JP | H09510192 | 2/1995 |
| JP | H10219289 | 8/1998 |
| JP | 2002037726 | 2/2002 |
| JP | 2003521570 | 7/2003 |
| JP | 2007055925 | 3/2007 |
| JP | 2012502963 | 2/2012 |
| JP | 2014507261 | 3/2014 |
| JP | 2016521764 | 7/2016 |
| WO | WO9401084 | 1/1994 |
| WO | WO9522958 | 8/1995 |
| WO | WO0142409 | 6/2001 |
| WO | WO2004009039 | 1/2004 |
| WO | WO2010034721 | 4/2010 |
| WO | WO2011120780 | 10/2011 |
| WO | WO2012089474 | 7/2012 |
| WO | WO2013175221 | 11/2013 |
| WO | WO2017182264 | 10/2017 |

OTHER PUBLICATIONS

Keltrol/Kelzan; Xanthan Gum Book; CPKelco; 2007; pp. 1-21; XP002769065.
Search Report and Written Opinion in PCTEP2018050207; Mar. 2, 2018.
IPRP1 in PCTEP2018050207, Aug. 13, 2019, EPO.
Search Report and Written Opinion in EP16190191; Nov. 23, 2016.
Search Report and Written Opinion in PCTEP2017073038; Dec. 11, 2017.
Written Opinion 2 in PCTEP2017073038; Aug. 14, 2018.
Written Opinion 3 in PCTEP2017073038; Jan. 3, 2019.
IPRP2 in PCTEP2017073038; Feb. 26, 2019.
Co-pending U.S. Appl. No. 16/334,954.
China Light Industry Association; Handbook of Technical Equipment in Light Industry; Aug. 31, 1997; pp. 1241, with English translation; vol. 3; China Machine Press; China.
Qiu Bingyi et al.; Science and Technology of Modern Cosmetics; Mar. 31, 2016; pp. 2253-2254, with English translation; Chinese Light Industry Press; China.
Liu Jing et al.; Principles of Food Engineering; Jan. 31, 2011; pp. 102, with English translation; China Metrology Press; China.
Opposition Notice in EP17764417 (EP3515400); Nov. 17, 2021; with English translation; European Patent Office (EPO).

* cited by examiner

XANTHAN STRUCTURED HIGH POLYOL LIQUID CLEANSERS

CROSS REFERENCE TO RELATED APPLICATIONS

The present application is a U.S. National Phase Application under 35 U.S.C. § 371 of International Application No. PCT/EP2018/050207, filed on Jan. 4, 2018, which claims priority to European Patent Application No. 17155142.7, filed on Feb. 8, 2017, the contents of which are incorporated herein in their entireties.

FIELD OF THE INVENTION

The present invention relates to personal care cleansing compositions comprising foaming, preferably mild, surfactants and high levels of polyol as moisturizing agent. It further related to a process for structuring such compositions with structurants typically incompatible with such systems.

BACKGROUND OF THE INVENTION

Personal care compositions (which generally refer to rinse-off or leave-on compositions suitable for application on mammalian, keratinous tissue) have been employed to cleanse and moisturize skin and/or hair, deliver actives, hide imperfections and to reduce oiliness/shine associated with sebum.

Consumers typically prefer compositions which are mild to the skin and/or deliver a moisturizing feel or other consumer benefits. Mildness, in turn, can be associated, for example, with lower levels of skin irritation, and lesser levels of water loss (as measured, for example, by Skicon and/or transepidermal water loss test known to those in the art).

One way of meeting these needs is by increasing the deposition of polyols such as glycerin; emollient oils, such as petrolatum or triglyceride oils; and, most preferably enhancement of both polyol and emollient oil deposition, preferably from a mild surfactant system.

Enhancement of polyols from a liquid cleanser can be achieved using high level of polyol together with specific mild surfactant(s) as described in EP 16190191.3 by Yang et all. They have found that, through the use of specific surfactants which are N-acyl derivatives of mono- and/or dicarboxylic acids, in combination with high glycerin, i.e. 40 to 90 wt. % containing compositions, it is possible to take advantage of the mild nature of the surfactants while providing enhanced glycerin deposition relative to the use of other types of surfactants in the same high glycerin systems.

Generally, high glycerin liquid cleanser compositions are known in the art.

U.S. Pat. No. 5,716,919 to Sano discloses a mild cleansing composition containing 25 to 80 wt. % of polyols, a nonionic surfactant and an anionic surfactant to remove cosmetic from the skin, which provides a fresh and clean after wash feel.

U.S. Pat. No. 6,303,108 to Roulier et al. claims an anhydrous solid self-warming foaming composition. 20 to 85 wt. % of polyol is used as binder of foaming surfactant powders to form the anhydrous solid foaming composition and provides a self-warming benefit.

U.S. Pat. No. 6,387,857 to Chambers et al claims a personal cleansing composition containing 30 to 50 wt. % of polyol to lower water activity of the cleanser composition for antimicrobial benefit.

U.S. Pat. No. 7,879,780 to Tsaur discloses a liquid cleansing composition comprising fatty acyl isethionate surfactant as the main surfactant and 10 to 60 wt. % of polyol such as glycerin or sorbitol. High level of polyol is used in the invention to stabilize the liquid cleanser composition under both high and low temperature storage conditions.

EP 1 237 534B1 to Masaaki et al discloses 10 to 50 wt. % of polyol to stabilize liquid cleanser composition containing mixture of sulfosuccinate surfactant and fatty acid soaps.

None of these references disclose high polyol levels (e.g., 40 to 75%, preferably 50 to 75% polyol) in cleansers structured by xanthan gum, a structurant normally incompatible with foaming liquid cleansers comprising such amounts of polyol. There is further no disclosure of a process for making such compositions.

Delivery of emollient oil from a liquid cleanser is also well known in the art. To stabilize the emollient oil droplets in liquid cleansers, polymers such as Carbopol, alkali soluble acrylic emulsions or xanthan gum are generally required to thicken and structure the liquid in order to stabilize the suspended oil particles. In the presence of high level of polyols and surfactants, polymeric thickeners are either not dissolved or are not fully swollen and are not able to provide the thickening efficiency due to low water activity. For example, xanthan gum is a widely used polysaccharide to thicken and structure aqueous system for food, skin care or personal cleansing applications. As described in Xanthan Book $8^{th}$ edition published by Kelco, xanthan gum is not compatible with aqueous solutions containing 40% by wt. or higher, preferably 50 wt. % or higher level of polyols. Its compatibility with surfactant solution ranges from 5 to 25 wt. % of surfactant depending on type of surfactant.

Unexpectedly, applicants have found that xanthan gum can be used to thicken and structure liquid cleansers containing high level of polyol while maintaining composition viscosity of 2000 cps or greater (e.g., 2000 cps to 15,000 cps), preferably 2500 cps or greater (e.g., 2500 to 10,000 cps), more preferably 3000 to 10,000 cps. using methods described in this patent. Applicants have further found a process for making such high-polyol compositions which are xanthan structured and maintain a minimum defined viscosity.

Xanthan gum as a structurant for liquid cleanser application is known and described in the prior art such as U.S. Pat. Nos. 4,728,457; 4,788,006, 5,948,739 and 6,001,344. None of these patents teach or disclose method to overcome compatibility problem of xanthan gum with foaming liquid cleansers containing 40% by wt. or higher level of polyols or compositions resulting thereof. Further, none of the references recognize that homogenization to produce xanthan gum of size 50 microns or less is required to resolve compatibility issues when used in high polyol systems.

SUMMARY OF THE INVENTION

In one form, the present invention provides personal care cleansing compositions, preferably cleansing compositions comprising foaming mild surfactant system wherein said composition comprises:

1) 40% to 75%, preferably 45% to 75%, preferably 50 to 75% by wt. polyol (preferably glycerine);
2) 1% to 15% of a surfactant selected from the group consisting of anionic surfactants, non-ionic surfactants, amphoteric surfactants, zwitterionic surfactants, cationic surfactants and mixtures thereof; salts of N-acyl derivatives of dicarboxylic amino acid (e.g., aspartic acid, glutamic acid) or salts of N-acyl derivatives of monocarboxylic acids (e.g., glycine alanine) and derivatives are particularly preferred;

3) 0.1% to 1.5%, preferably 0.3% to 1.2% xanthan gum;
4) 10% to 50% water; and
5) wherein viscosity of final composition is 2000 to 15,000 cps, preferably 3000 to 10,000 cps, as measured using #5 spindle at 20 rpm for 30 seconds.

Preferably, the xanthan gum particles have a size of 50 microns or less, preferably 0.1 to 50 microns, preferably 0.5 to 40 microns.

If present, the N-acyl amino acid surfactants preferably comprise the majority of the surfactant system, e.g., 50% to 100% of the surfactant system, or 60% to 100%, or 70% to 100% of the surfactant system.

In a second form, the invention relates to a process for making a composition comprising:

1) 40% to 75%, preferably 45% to 75% polyol (preferably glycerine);
2) 1% to 15% of a surfactant selected from the group consisting of anionic surfactants, non-ionic surfactants, amphoteric surfactants, zwitterionic surfactants, cationic surfactants and mixtures thereof; salts of N-acyl derivatives of dicarboxylic amino acid (e.g., aspartic acid, glutamic acid) or salts of N-acyl derivatives of monocarboxylic acids (e.g., glycine alanine) and mixtures of such derivatives are particularly preferred;
3) 0.1% to 1.5%, preferably 0.3% to 1.2% xanthan gum;
4) 10% to 50% water;
5) wherein viscosity of final composition is 2000 to 15,000 cps, preferably 3000 to 10,000 cps, as measured using #5 spindle at 20 rpm for 30 seconds, wherein preferably xanthan gum particles have size of 0.1 to 50 microns or 0.5 to 40 microns; and wherein, if present, the N-acyl amino acid surfactants preferably comprise the majority of the surfactant system, e.g., 50% to 100% of the surfactant system, or 60% to 90%, or 70% to 100% of the surfactant system.

wherein said process comprises:

1) adding and mixing all xanthan gum with 5 to 10 parts of polyol (preferably glycerin) to form a uniform mixture;
2) separately adding and mixing balance of polyol, surfactant and water in a separate mixer (e.g., main mixer);
3) adding the xanthan gum in polyol mixture of (1) to the mixture of (2) and homogenizing the mixture of (1) and (2) with suitable homogenization (e.g., using rotor-stator device based on revolutions per minute (rpm) or homogenizer based on pressure) such that xanthan particles in final mix have size of 50 microns or less, preferably 0.5 to 40 microns.

A homogenizer which may be used, for example, is in a rotor-stator mechanical homogenizer at a homogenization speed greater than 500 rpm, preferably 1500 rpm to 15,000 rpm for, for example, four minutes or greater depending on the diameter of the rotor and its rotational speed, the distance between the rotor and the stator, the time in the mixer, and the number of generators in the series. Variables include the number of rows of teeth, their angle, and the width of the openings between teeth. Final xanthan gum particle size will depend on both the homogenization speed and mixing time. In general, higher homogenization speed and/or longer mixing time will create smaller xanthan gum particles.

In another form, the process may comprise forming a concentrated xanthan gum pre-dispersion comprising all of xanthan gum with part of surfactant, polyol and water; homogenizing the pre-dispersion (again using rotor-stator mixer or homogenizer based on pressure) to obtain xanthan particles of 50 microns or less, preferably 0.5 to 40 microns; and then mixing with other remaining ingredients. The process comprises:

1) premixing 4 to 8 wt % of xanthan gum with 10 to 20 wt % of polyol;
2) adding and mixing the xanthan and polyol mixture to 75 to 90 wt % surfactant solution with total surfactant level being higher than 15 wt %, preferably higher than 20%;
3) homogenizing the predispersion of (1) plus (2) under homogenization conditions sufficient to obtain xanthan particles of 50 micron or less, preferably 0.5 to 40 microns or less (again, an example of such condition is to homogenize the predispersion at greater than 500 rpm for four minutes or greater); and 4) adding and mixing the xanthan gum predispersion of (3) to a mixer containing the rest of the ingredients, said mixing preferably being for over 5 minutes.

DETAILED DESCRIPTION OF THE INVENTION

Except in the examples, or where otherwise explicitly indicated, all numbers in this description indicating amounts of material or conditions of reaction, physical properties of materials and/or use are to be understood as modified by the word "about." All amounts are by weight of the final composition, unless otherwise specified.

It should be noted that in specifying any range of concentration or amount, any particular upper concentration can be associated with any particular lower concentration or amount.

For the avoidance of doubt, the word "comprising" is intended to mean "including" but not necessarily "consisting of" or "composed of." In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

The present invention provides compositions comprising high levels of polyol, preferably glycerine, in which xanthan gum surprisingly can be used as a structurant and provide good viscosity. Specifically, applicants have found that, by preparing in a particular manner (using homogenization), novel compositions can be obtained.

More particularly, novel compositions of the invention comprise:

1) 40% to 75%, preferably 45% to 75%, more preferably 50 to 75% by wt. polyol (preferably glycerine);
2) 1% to 15% of a surfactant selected from the group consisting of anionic surfactants, non-ionic surfactants, amphoteric surfactants, zwitterionic surfactants, cationic surfactants and mixtures thereof; salts of N-acyl derivatives of dicarboxylic amino acid (e.g., aspartic acid, glutamic acid) or salts of N-acyl derivatives of monocarboxylic acids (e.g., glycine alamine) and derivatives are particularly preferred;
3) 0.1% to 1.5%, preferably 0.3% to 1.2% xanthan gum;
4) 10% to 50% water; and
5) wherein viscosity of final composition is 2000 to 15,000 cps, preferably 3000 to 10,000 cps, as measured using #5 spindle at 20 rpm for 30 seconds.

Preferably, the xanthan gum particles have a size of 50 microns or less, preferably 0.1 to 50 microns, preferably 0.5 to 40 microns.

Compositions of the invention comprise, as noted, 40 to 75%, preferably 45 to 75% polyol. While glycerine is preferred polyol, other polyols may be used. These include sorbitol, propylene glycol, polypropylene glycol and mixtures thereof (including preferably, mixtures of one of these with glycerine).

The lower level of polyol used may be 40 or 45 or 50% (and all digits between) and is preferably 51% and higher, including 51 to 60 and all digits between. The upper range may be 60 to 75 and all digits in between. Of course, any digit between 41 and 74 can theoretically be upper or lower limit. For example, 74% can be the lower limit and 75% can be the upper limit.

It is unexpected that xanthan gum would be compatible with such high polyol systems. However, applicants have further discovered a process which permits such compositions while maintaining excellent viscosity. It is not recognized that xanthan needs to be homogenized (by which we mean broken down, whether in a rotor-stator mechanical mixer using rpm; or in a "classic" homogenizer using pressure through an inlet to homogenize) to small particle size to obtain the noted compatibility.

Surfactant

The composition may further comprise 1 to 15%, preferably 2 to 12%, even more preferably 2 to 9% by wt. surfactant selected from the group consisting of anionoic surfactants, non-ionic surfactants, amphoteric surfactants, zwitterionic surfactants, cationic surfactants and mixtures thereof.

The anionic detergent active which may be used in the invention may be aliphatic sulfonates, such as a primary alkane (e.g., $C_8$-$C_{12}$) sulfonate, primary alkane (e.g., $C_8$-$C_{22}$ disulfonate, $C_8$-$C_{22}$ alkene sulfonate, $C_8$-$C_{22}$ hydroxyalkane sulfonate or alkyl glyceryl ether sulfonate (AGS); or aromatic sulfonates such as alkyl benzene sulfonate. The anionic may also be an alkyl sulfate (e.g., $C_{12}$-$C_{18}$ alkyl sulfate) or alkyl ether sulfate (including alkyl glyceryl ether sulfates).

Solubilizing cation may include sodium, potassium, ammonium or substituted ammonium. Ammonium and sodium lauryl ether sulfates are preferred. The anionic may also be alkyl sulfosuccinates (including mono- and dialkyl, e.g., $C_6$-$C_{22}$ sulfosuccinates); alkyl and acyl taurates, alkyl and acyl sarcosinates, sulfoacetates, $C_8$-$C_{22}$ alkyl phosphates and phosphates, alkyl phosphate esters and alkoxyl alkyl phosphate esters, acyl lactates, $C_8$-$C_{22}$ monoalkyl succinates and maleates, sulphoacetates, alkyl glucosides and acyl isethionates, and the like. Sulfosuccinates may be monoalkyl sulfosuccinates having the formula:

$R^4O_2CCH_2CH(SO_3M)CO_2M$; and amide-MEA sulfosuccinates of the formula;

$R^4CONHCH_2CH_2O_2CCH_2CH(SO_3M)CO_2M$ wherein $R^4$ ranges from $C_8$-$C_{22}$ alkyl and M is a solubilizing cation.

Sarcosinates are generally indicated by the formula:

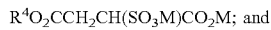
$R^1CON(CH_3)CH_2CO_2M$, wherein $R^1$ ranges from $C_8$-$C_{20}$ alkyl and M is a solubilizing cation.

Taurates are generally identified by formula:

$R^2CONR^3CH_2CH_2SO_3M$ wherein $R^2$ ranges from $C_8$-$C_{20}$ alkyl, $R^3$ ranges from $C_1$-$C_4$ alkyl and M is a solubilizing cation.

The inventive cleansing composition may contain $C_8$-$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms. The acyl isethionate may be an alkoxylated isethionate such as is described in Ilardi et al., U.S. Pat. No. 5,393,466, titled "Fatty Acid Esters of Polyalkoxylated isethonic acid; issued Feb. 28, 1995; hereby incorporated by reference. This compound has the general formula:

RC—O(O)—C(X)H—C(Y)H$_2$—(OCH—CH$_2$)$_m$—SO$_3$M$^+$ wherein R is an alky I group having 8 to 18 carbons, m is an integer from 1 to 4, X and Y are hydrogen or an alkyl group having 1 to 4 carbons and M is a monovalent cation such as, for example, sodium, potassium or ammonium.

Amphoteric Surfactants

One or more amphoteric surfactants are used in this invention. Such surfactants include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

$R^1$—[—C(O)—N H(CH$_2$)$_n$—]$_m$—N—(R$^2$)(R$^3$)X—Y where $R^1$ is alkyl or alkenyl of 7 to 18 carbon atoms;
$R^2$ and $R^3$ are each independently alkyl, hydroxyalkyl or carboxyalkyl of 1 to 3 carbon atoms;
n is 2 to 4;
m is 0 to 1;
X is alkylene of 1 to 3 carbon atoms optionally substituted with hydroxyl,
Y is —CO$_2$— or —SO$_3$—

Suitable amphoteric surfactants within the above general formula include simple betaines of formula:

$R^1$—N$^+$—(R$^2$)(R$^3$)CH$_2$CO$_2$— and amido betaines of formula:

$R^1$—CONH(CH$_2$)$_n$—N$^+$—(R$^2$)(R$^3$)CH$_2$CO$_2$— wherein n is 2 or 3.

In both formulae $R^1$, $R^2$ and $R^3$ are as defined previously. $R^1$ may in particular be a mixture of $C_{12}$ and $C_{14}$ alkyl groups derived from coconut oil so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula:

$R^1$—N$^+$—(R$^2$)(R$^3$)(CH$_2$)SO$_3$— or $R^1$—CON H(CH$_2$)$_m$—N+—(R$^2$)(R$^3$)(CH$_2$)SO$_3$— where m is 2 or 3, or variants of these in which —(CH$_2$)$_3$SO$_3$ is replaced by

—CH$_2$C(OH)(H)CH$_2$SO$_3$—

In these formulae $R^1$, $R^2$ and $R^3$ are as discussed previously.

Amphoacetates and diamphoacetates are also intended to be covered in possible zwitterionic and/or amphoteric compounds which may be used such as e.g., sodium lauroamphoacetate, sodium cocoamphoacetate, and blends thereof, and the like.

Nonionic Surfactants

One or more nonionic surfactants may be used in the cleansing composition of the present invention. The nonionics which may be used include in particular the reaction products of compounds having a hydrophobic group and a reactive hydrogen atom, for example aliphatic alcohols, acids, amides or alkylphenols with alkylene oxides, especially ethylene oxide either alone or with propylene oxide. Specific nonionic detergent compounds are alkyl ($C_6$-$C_{22}$) phenols ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxide, and the like.

In some forms, the compositions of the invention may comprise a surfactant selected from the group consisting of salts of N-acyl derivatives of dicarboxylic amino acid (e.g., asparatic acid, glutamic acids), salts of N-acyl derivatives of monocarboxylic acids (e.g., glycine, alanine, sarcosine) and mixtures of such derivatives of mono- and dicarboxylic acids; Preferred di-carboxylic amino acid surfactants are acylglutamate and acylaspartate surfactants. Preferred mono-carboxylic amino acid surfactants are acylglycinate, acylalanate, and acyl sarcosinate. Preferably, these are potassium and/or sodium salts of N-acyl derivatives of amino acids.

There are typically two formats of amino acid surfactants commercially available. One is powder or flake format, which is typically more expensive and high in purity. Examples of solid dicarboxylic amino acid surfactants include:

sodium N-cocoyl-L-glutamate (e.g., Amisoft® CS-11 by Ajinomoto)
sodium N-lauroyl-L-glutamate (e.g., Amisoft® LS-11 by Ajinomoto)
sodium N-myristoyl-L-glutamate (Amisoft® MS-11 by Ajinomoto)
potassium N-cocoyl_l-Glutamate (e.g., Amisoft® CK-11 by Ajinomoto)
potassium N-myristoyl-L-glutamate (Amisoft® MK-11 by Ajinomoto)
potassium N-lauroyl-L-glutamate (Amisoft® LK-11 by Ajinomoto)
Sodium Lauroyl Aspartate (AminoFoamer™ FLMS-P1 by Asahi Kasei Chemical Corporation)
Sodium Lauroyl Glutamate (Aminosurfact™ ALMS-P1/S1 by Asahi Kasei Chemical Corporation)
Sodium Myristoyl Glutamate (Aminosurfact™ AMMS-P1/S1 by Asahi Kasei Chemical Corporation)

Examples of solid monocarboxylic amino acids surfactants include:

sodium cocoyl glycinate (e.g., Amilite® GCS-11 by Ajinomoto)
potassium cocoyl glycinate (e.g., Amilite® GCK-11 by Ajinomoto Preferably the N-acyl amino acid surfactant derivatives comprise 50 to 100% of total surfactant system.

The compositions further comprise 0.1 to 1.5% by wt., preferably 0.3% to 1.2% by wt. xanthan gum. Xanthan gums are polysaccharides which can be synthesized by fermentation of certain sugars by microorganisms such as the bacterium *Xanthomonas campestris*. Xanthan consists of repeating pentasaccharide units consisting of two D-glucopyranosyl units, two D-mannopyranosyl units, and one D-glucopyranosyluronic acid unit with molecular weight of from 1 million to 50 million. Xanthan gums have been widely used to thicken or stabilize aqueous system due to its excellent compatibility with many chemicals such as salts, acids, bases and water-mixable solvents. Xanthan gums preferred for the invention are commercial products, such as Keltrol CG-T, Keltrol CG-SFT or Keltrol-CG manufactured by Kelco, Vangan NF-C available from Vanderbilt and Minerals.Rhodopol 23 C from Solvay As indicated, xanthan would not normally be incorporated as a structurant in high polyol systems especially together with surfactants as claimed in this invention. However, because of the novel processing step of our invention, applicants can make high polyol and xanthan gum systems which permits xanthan to enhance viscosity of personal liquid cleanser as claimed. The key is the recognition that xanthan gum particles must have size of 50 microns or less to ensure compatibility in such high polyol systems.

The composition further comprises 10 to 50%, preferably 15 to 40% water.

In a second form, the invention comprises a process which permits novel compositions of the invention to be made.

Specifically, this invention relates to homogenization process (as noted earlier, "homogenization" refers to both breaking up by rotor-stator mechanical device used at certain rpm and/or by "classic" homogenizer which is based on pressure feeding) for making a composition comprising:
1) 40% to 75%, preferably 45% to 75%, more preferably 50 to 75% by wt. polyol (preferably glycerine);
2) 1% to 15% of a surfactant selected from the group consisting of anionic surfactants, non-ionic surfactants, amphoteric surfactants, zwitterionic surfactants, cationic surfactants and mixtures thereof; salts of N-acyl derivatives of dicarboxylic amino acid (e.g., aspartic acid, glutamic acid) or salts of N-acyl derivatives of monocarboxylic acids (e.g., glycine alamine) and mixtures of such derivatives are particularly preferred;
3) 0.1% to 1.5%, preferably 0.3% to 1.2% xanthan gum;
4) 10% to 50% water; and
wherein viscosity of final composition is 2000 to 15,000 cps, preferably 3000 to 10,000 cps, as measured using #5 spindle at 20 rpm for 30 seconds; wherein preferably xanthan gum particles have size of 0.1 to 50 microns or 0.5 to 40 microns; and wherein, if present, the N-acyl amino acid surfactants preferably comprise the majority of the surfactant system, e.g., 50% to 100% of the surfactant system, or 60% to 100%, or 70% to 10% of the surfactant system.

wherein said process comprises:
1) adding and mixing all xanthan gum with 5 to 10 parts of polyol (preferably glycerin) to form a uniform mixture;
2) separately adding and mixing balance of polyol, surfactant and water in separate mixer (e.g., main mixer);
3) adding xanthan gum in polyol mixture of (1) to the mixture of (2) and homogenizing the mixture of (1) and (2) with suitable homogenization such that xanthan particles in final mix have size of 50 microns or less, preferably 0.5 to 40 microns.

A homogenizer which may be used is a rotor-stator mechanical homogenizer at ahomogenization speed greater than 500 rpm, preferably 1500 rpm to 15,000 rpm for, for example, four minutes or greater.

In another form, the process may comprise forming a concentrated xanthan gum pre-dispersion comprising all of xanthan gum with part of surfactant, polyol and water; homogenizing the pre-dispersion (using rotor-stator mixer or homogenizer based on pressure) to obtain xanthan particles of 50 microns or less, preferably 0.5 to 40 microns; and then mixing with other remaining ingredients. The process comprises:

1) premixing 4 to 8 wt % of xanthan gum with 10 to 20 wt % of polyol;
2) adding and mixing the xanthan and polyol mixture to 75 to 90 wt % surfactant solution with total surfactant level higher than 15 wt %, preferably higher than 20%;
3) homogenizing the predispersion of (1) plus (2) under conditions sufficient to obtain xanthan particles of 50 microns or less, preferably 0.5 to 40 microns; and
4) adding and mixing the xanthan gum predispersion of (3) to a mixer containing the rest of the ingredients, mixing preferably being or over 5 minutes.

Homogenization is a process using a device (e.g., rotor-stator or classic homogenizer as noted above) to break down the xanthan gum particles, typically having particle size between 100 to 400 micrometers, in the said high-polyol containing personal liquid cleanser to form fine xanthan gum dispersion with size 50 microns or less than, more preferably 0.5 to 40 microns. Many different lab and industry homogenizers using various physical technologies to micronize particles in a liquid can be used for this invention. For example, Silverson Mixer Homogenizers are well known rotor-stator mechanical homogenizers known in the industry, and Sonolator® is an in-line, high-pressure homogenizer also known in the industry.

Pro300D homogenizer, which was used to make examples of this invention is a rotor-stator mechanical homogenizer from PRO Scientific.

EXAMPLES

Examples 1 and 2 and Comparative A to F

The effect of xanthan gum process on liquid cleanser viscosity containing various levels of glycerin is shown in Table 1 above. All samples were prepared using the process described below except at end of processing. First, 6 parts of glycerin (polyol) was weighed and saved in a beaker. All the surfactants, water, and the rest of the glycerin were added to the main mixer and mixed to uniformity for about 10 minutes using an overhead mixer equipped with a 3-blade propeller at room temperature. Xanthan gum and Jaguar C17 powders were added and dispersed to the 6 parts of glycerin saved in the beaker. The xanthan gum dispersion was then added to the main mixer and mixed for 5 minutes at room temperature. Perfume and phenoxyethanol were added and mixed for another 5 minutes. The pH of the cleanser was adjusted to a range of 5.9 to 6.3 using 50 wt. % citric acid or 25 wt % NaOH solution.

After all the ingredients were added and the pH of the liquid was adjusted, Examples 1 to 2 and Comparative A were homogenized using a Pro300D from Pro Scientific Inc. at 5500 rpm for 5 to 7 minutes. Comparative examples B and C (with composition similar to those of Examples 1 to 2 and Comparative A) were mixed using an overhead mixer equipped with a 3-blade propeller mixed at 700-750 rpm for 10 minutes. Comparative A was mixed in homogenizer, but is considered a comparative because it uses much lower level of polyol. Viscosity of the prepared liquid was measured about 2 hours after the preparation using a Brookfield Rheometer with number 5 spindle at 20 rpm for 30 seconds. The results are given in Table 1. The results clearly shows that xanthan gum processing has a large effect on the liquid viscosity for high polyol (e.g., glycerin) containing liquids. For liquids with a high level of glycerin, Example 1 and 2, the homogenization process gives significantly higher viscosity compared to similar liquid mixed using overhead mixer (Comparative B and C). For liquids with low level of glycerin (Comparative A and Comparative D), the mixing method does not show much difference in final viscosity. It's surprising to find that Examples 1 and 2, with high glycerin, have significantly higher viscosity compared to Compara-

TABLE 1

Effect of polyol level and processing on liquid cleanser viscosity

| | Examples Prepared by homogenization process | | Comparative examples Prepared by overhead mixing process (except A) | | | | | |
|---|---|---|---|---|---|---|---|---|
| | Example 1 | Example 2 | Comp. A | Comp. B | Comp. C | Comp. D | Comp. E | Comp. F |
| Na cocoamidopropyl betaine | 1.5 | 1.5 | 1.5 | 1.5 | 1.5 | 1.5 | 1.5 | 1.5 |
| Na lauroyl glutamate | 4.5 | 4.5 | 4.5 | 4.5 | 4.5 | 4.5 | 4.5 | 4.5 |
| Xanthan gum Keltrol CG-SFT | 0.6 | 0.6 | 0.6 | 0.6 | 0.6 | 0.6 | — | — |
| Carbopol Aqua SF1 | — | — | — | — | — | — | 0.9 | — |
| Hydroxyethyl cellulose Methocel 40-100 | — | — | — | — | — | — | — | 0.9 |
| Glycerin | 70 | 50 | 6 | 70 | 50 | 6 | 70 | 70 |
| Guar Hydroxypropyltrimonium Chloride Jaguar C17 | 0.06 | 0.06 | 0.06 | 0.06 | 0.06 | 0.06 | 0.06 | 0.06 |
| Perfume | 0.8 | 0.8 | 0.8 | 0.8 | 0.8 | 0.8 | 0.8 | 0.8 |
| Phenoxyethanol | 0.6 | 0.6 | 0.6 | 0.6 | 0.6 | 0.6 | 0.6 | 0.6 |
| pH | 6.04 | 6.08 | 6.20 | 6.10 | 6.05 | 5.95 | 6.50 | 6.10 |
| Viscosity, cps (centipoises) Brookfield Rheometer # 5 spindle 20 rpm, 30 sec; cps | 5020 | 7040 | 2340 | 330 | 1540 | 1940 | 125 | Polymer precipitated at bottom | tive A, with low level of glycerin, when both are using the homogenization process. Using the process of this invention, compatability problem of xanthan gum with high glycerol containing liquid cleanser can be resolved; and the efficiency of the gum to thicken the liquid cleanser is also dramatically enhanced.

Two other examples, Comparative example E and F, were also prepared using other conventional polymeric thickeners, Carbopol Aqua SF1 and Methocel 40-100, for comparison. Both samples were prepared using overhead mixer equipped with a 3-blade propeller and the same procedure described above without homogenization. The viscosity of Aqua SF1 sample as shown in the table is very low, 125 cps, compared to Example 1 of this invention even though higher level of polymer is used than of xanthan gum (0.9% versus 0.6%). The sample containing Methocel 40-100 showed phase separation 2 hours after the preparation. Methocel 40-100 precipitated out of the liquid and formed sticky, gluey lumps at the bottom of the liquid during storage.

Examples 3A to 3F: Effect of Homogenization Speed and Time

TABLE 2

Effect of homogenization speed and time on liquid cleanser viscosity

| | Example 3A | Example 3B | Example 3C | Example 3D | Example 3E |
|---|---|---|---|---|---|
| Homogenization speed and time of xanthan gum in surfactant pre-dispersion | | | | | |
| Mixing speed | 5600 rpm | 5600 rpm | 5600 rpm | 4500 rpm | 3000 rpm |
| Mixing time | 1 min | 3 min | 6 min | 3 min | 3 min |
| Final liquid viscosity | | | | | |
| Brookfield Rheometer; #5 spindle, 20 rpm, 30 sec | | | | | |
| Viscosity (cps) Same day after preparation | Viscosity is too low to measure. | 3380 | 4470 | 3520 | 3580 |
| Viscosity (cps) Aged 5 day at RT | Xanthan gum gel precipitate to bottom of the product. | 4440 | 4780 | 4150 | 4280 |

Five (5) samples with compositions same as Example 1 were prepared using xanthan gum in surfactant pre-dispersion instead of adding all the ingredient to the mixer and homogenizing the whole batch as described in Example 1. This is the second defined process of the invention. Detail of the procedure is described below.

First, a glutamate/betaine surfactant premix containing 17.8 wt. % Na lauroyl glutamate and 5.93 Na cocoylpropylbetaine with a pH about 5.9 was prepared. Six (6) parts of xanthan gum powder was mixed with 18 parts of glycerin. The mixture was then added to 76 parts of glutamate/betaine surfactant premix, and homogenized at various speed and time as given in Table 2 (e.g., 3000 to 5600 rpm) using Pro300D homogenizer to make the xanthan gum in surfactant pre-dispersion.

The final composition was then prepared by adding 68.2 parts of glycerin, 0.05 parts of Jaguar C17, 2.48 parts of deionized water, 17.68 parts of glutamate/betaine surfactant premix described above, 1 parts of perfume and 0.6 parts of phenoxyethanol to a mixer equipped with an overhead mixer. The mixture was mixed using 3-blade propeller at 600 rpm for 10 minutes, following the addition of 10 parts of xanthan gum in surfactant predispersion prepared above. The mixing was continued for another 10 minutes at 600-700 rpm. Viscosity of the liquid was measured about 2 hour after the preparation, and also re-measured 5 days after the preparation. Both data are shown in Table 2. The viscosity data shows that the homogenization process is very robust in controlling the final viscosity of the liquid cleanser. With sufficient mixing, all the liquids have similar viscosity after 5 days storage at room temperature.

Examples 4 to 6

TABLE 3

| | Example 4 | Example 5 | Example 6 |
|---|---|---|---|
| Na cocoamidopropyl betaine | 2.25 | 1.5 | 1.5 |
| Na lauroyl glutamate | 6.75 | 4.5 | 4.5 |
| Glycerin | 60 | 50 | 50 |
| Guar Hydroxypropyltrimonium Chloride Jaguar C17 | 0.1 | 0.1 | 0.1 |
| Xanthan gum Keltro CG-SFT | 1.0 | 0.8 | 0.8 |
| Petrolatum | — | 5 | — |
| Sunflower seed oil | — | — | 5 |
| Perfume | 1.0 | 1.0 | 1.0 |

TABLE 3-continued

| | Example 4 | Example 5 | Example 6 |
|---|---|---|---|
| Glydant plus | 0.3 | 0.3 | 0.3 |
| Deionized water | To 100 | To 100 | To 100 | pH of the liquid: 5.9 to 6.2

Examples 4, 5 and 6 of this invention with composition as shown in Table 3 were prepared using the xanthan gum in surfactant pre-dispersion process described in Example 3 above. Example 4 contains high level of total surfactant compared to Example 1, 9% vs. 6%. Examples 5 and 6 contain emollient oil, petrolatum and sunflower seed oil respectively. Both oils were added after the addition of xanthan gum in surfactant pre-dispersion and mixed at 700-750 rpm for 10 minutes. Example 5 containing petrolatum was process at 50 C, and Example 6 containing sunflower seed oil was mixed at room temperature. All the samples are viscous and well structured. Both petrolatum and sunflower seed oil are stably suspended in the liquid cleanser without phase separation at both high and low temperature storage condition.

The invention claimed is:

1. A composition comprising:
   a) 65% to 75% by wt. polyol;
   b) 1% to 15% by wt. of a surfactant selected from the group consisting of anionic surfactants, non-ionic surfactants, amphoteric surfactants, zwitterionic surfactants, cationic surfactants and mixtures thereof;
   c) 0.1% to 1.5% by wt. xanthan gum;
   d) 10% to 50% by wt. water; and
   e) wherein viscosity of final composition is 3000 to 15,000 cps as measured using #5 spindle at 20 rpm for 30 seconds;
   f) wherein xanthan gum is in the form of particles having a size of 50 microns or less.

2. The composition according to claim 1, wherein said surfactant comprises a surfactant selected from the group consisting of salts of N-acyl derivatives of dicarboxylic, or salts of N-acyl derivatives of monocarboxylic acid and mixtures thereof.

3. The composition according to claim 1, wherein polyol is glycerin.

4. The composition according to claim 1, wherein the composition comprises 68% to 75 wt % polyol.

5. The composition according to claim 4, wherein the composition comprises 70% to 75 wt % polyol.

6. A process for making a composition comprising:
   a) 65% to 75% by wt. polyol;
   b) 1% to 15% by wt. of a surfactant selected from the group consisting of anionic surfactants, non-ionic surfactants, amphoteric surfactants, zwitterionic surfactants, cationic surfactants and mixtures thereof;
   c) 0.1% to 1.5% by wt. xanthan gum;
   d) 10% to 50% by wt. water; and
   e) wherein viscosity of final composition is 3000 to 15,000 cps as measured using #5 spindle at 20 rpm for 30 seconds
   f) wherein xanthan gum is in the form of particles having a size of 50 microns or less wherein said process comprises:
      1) adding and mixing all xanthan gum with 5 to 10 parts of polyol to form a uniform mixture;
      2) separately adding and mixing balance of polyol, surfactant and water in a separate mixer;
      3) adding the xanthan gum in polyol mixture of (1) to the mixture of (2) and homogenizing the mixture of (1) and (2) with suitable homogenization such that xanthan particles in final mix have size of 50 microns or less.

7. A process according to claim 6, wherein homogenization is with a rotor-stator mixer and is conducted at homogenization speed greater than 500 rpm for four minutes or greater.

8. A process according to claim 6 wherein surfactant of (2) comprises a surfactant selected from the group consisting of salts of N-acyl derivatives of dicarboxylic, or salts of N-acyl derivatives of moncarboxylic acid and mixtures thereof.

9. A process according to claim 6, wherein polyol is glycerin.

10. A process for making a composition comprising:
    a) 65% to 75% by wt. polyol;
    b) 1 to 15% by wt. of a surfactant selected from the group consisting of anionic surfactants, non-ionic surfactants, amphoteric surfactants, zwitterionic surfactants, cationic surfactants and mixtures thereof;
    c) 0.1% to 1.5% by wt. xanthan gum;
    d) 10% to 50% by wt. water; and
    e) wherein viscosity of final composition is 3000 to 15,000 cps as measured using #5 spindle at 20 rpm for 30 seconds
    f) wherein xanthan gum is in the form of particles having a size of 50 microns or less wherein said process comprises:
       1) premixing 4 to 8 wt % of xanthan gum with 10 to 20 wt % of polyol;
       2) adding and mixing the xanthan and polyol mixture to 75 to 90 wt % surfactant solution with total surfactant level being higher than 15 wt %, preferably higher than 20%;
       3) homogenizing the predispersion of (1) plus (2) under homogenization conditions sufficient to obtain xanthan particles of 50 microns or less; and
       4) adding and mixing the xanthan gum predispersion of (3) to a mixer containing the rest of the ingredients, said mixing being for over 5 minutes.

11. A process according to claim 10 wherein homogenization is with a rotor-stator mixer and is conducted at homogenization speed greater than 500 rpm for four minutes or greater.

* * * * *